United States Patent [19]

Adair

[11] Patent Number: 5,704,892
[45] Date of Patent: *Jan. 6, 1998

[54] ENDOSCOPE WITH REUSABLE CORE AND DISPOSABLE SHEATH WITH PASSAGEWAYS

[76] Inventor: Edwin L. Adair, 317 Paragon Way, Castle Pines Village, Colo. 80104

[ * ] Notice: The term of this patent shall not extend beyond the expiration date of Pat. No. 5,402,768.

[21] Appl. No.: 375,934

[22] Filed: Mar. 15, 1996

Related U.S. Application Data

[63] Continuation-in-part of Ser. No. 80,323, Jun. 22, 1993, Pat. No. 5,402,768, which is a continuation-in-part of Ser. No. 938,629, Sep. 1, 1992, abandoned.

[51] Int. Cl.$^6$ ................................................ A61B 1/04
[52] U.S. Cl. ...................... 600/121; 600/120; 600/177; 600/162
[58] Field of Search ........................... 600/121, 123, 600/125, 171, 172, 173, 175, 176, 182, 177; 604/263

[56] References Cited

U.S. PATENT DOCUMENTS 5,402,768  4/1995  Adair ............................................. 128/4
5,573,493  11/1996  Sauer et al. ............................... 600/121

*Primary Examiner*—Beverly M. Flanagan
*Attorney, Agent, or Firm*—Fields & Johnson, P.C.

[57] ABSTRACT

An improved endoscope has been provided which includes an elongated cylindrical shell housing with a transparent window at the distal end thereof. A removable core has an objective endoscope lens or optics at the distal end thereof and an image sensor mounted within the distal end of the core. A transmitting electronic cable with multiple conductors each has a distal end connected to the image sensor circuit board and a proximal end connected to a video control unit. Signals are transmitted from the control unit to the video monitor which displays the image. A sterile separable channel section, removably receives the core in a defined relationship and has at least one longitudinal channel for transmitting fluids or for receiving an operative instrument or carrying light transmitting fiber. A flexible tube is connected to the proximal end of the channel for supplying fluid or for manipulating the operative instrument from a remote location. The separable channel section is disposable after use on a patient. Light transmitting fibers can be integral with the housing or core or inserted into at least one of the channels in the channel or sheath section.

20 Claims, 5 Drawing Sheets

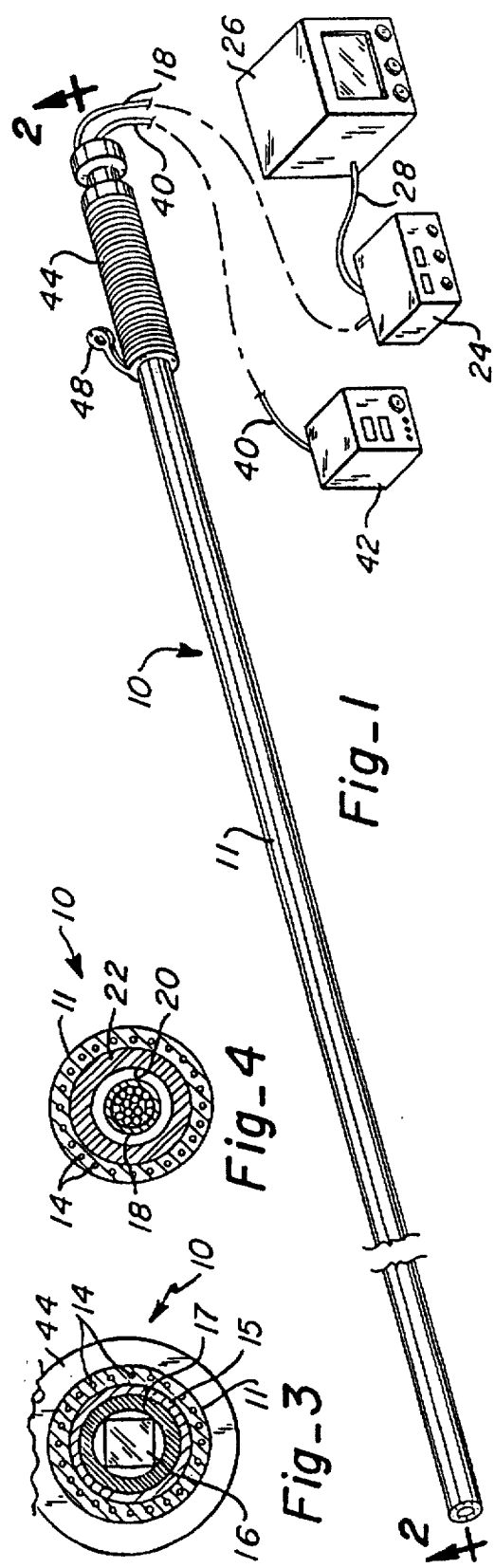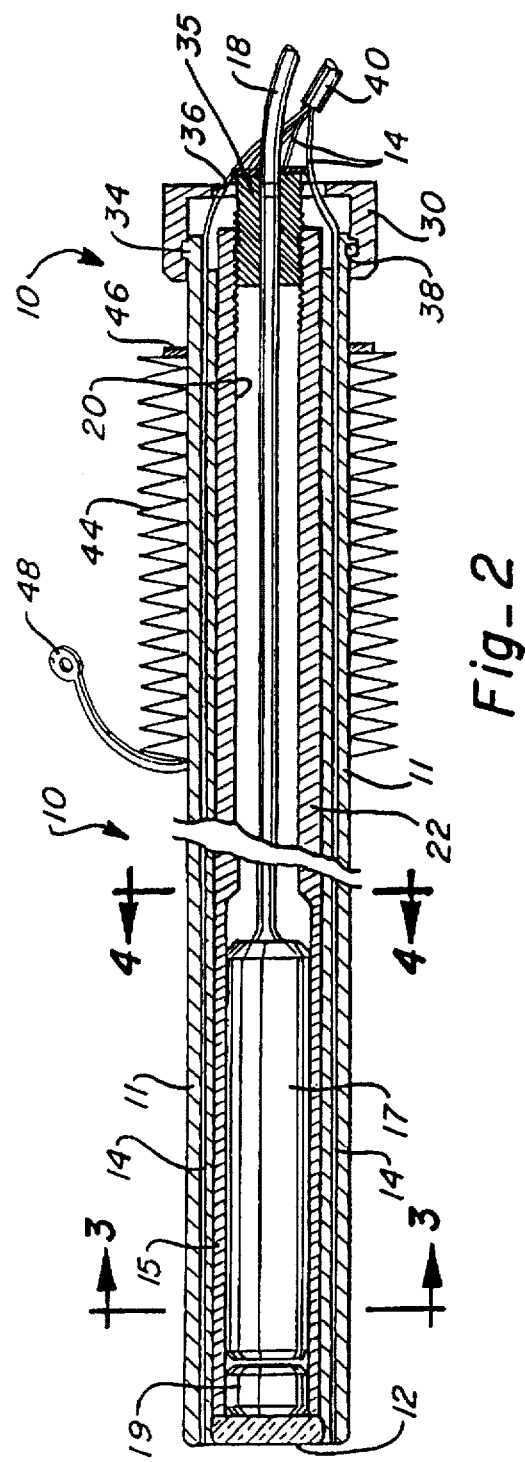

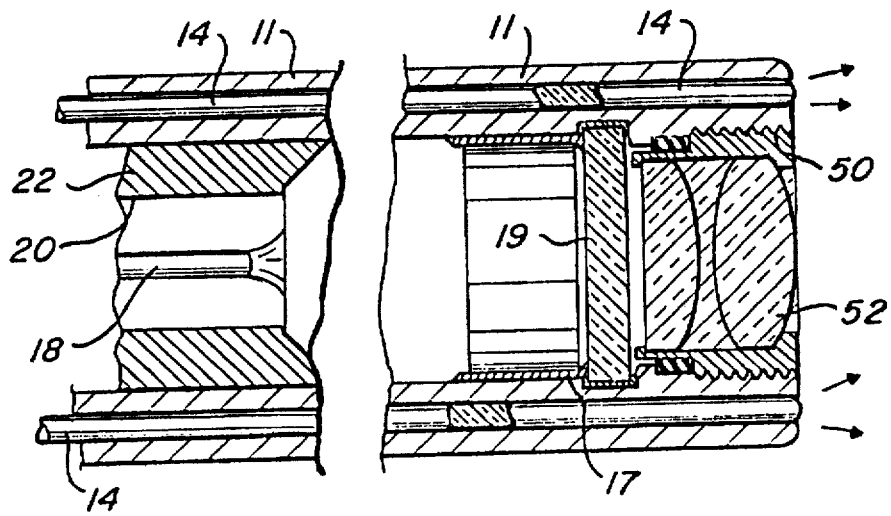
Fig_5
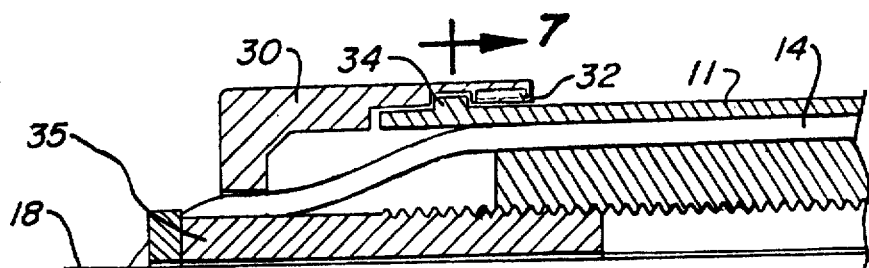
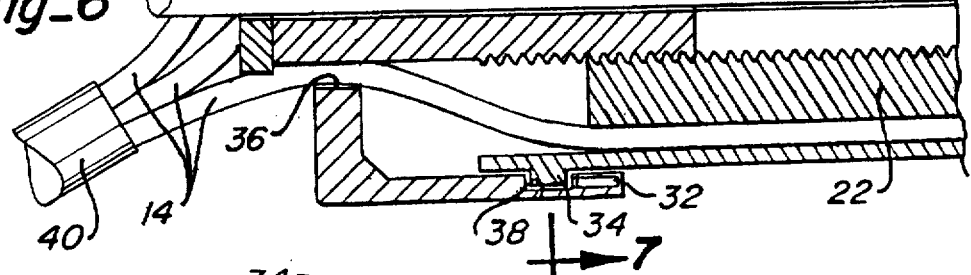
Fig_6
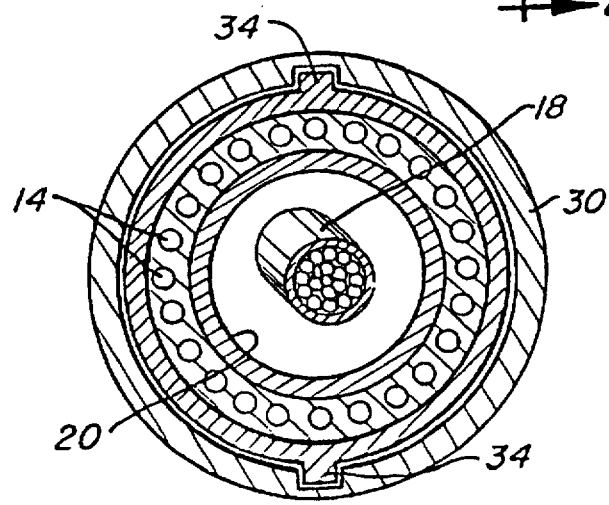
Fig_7

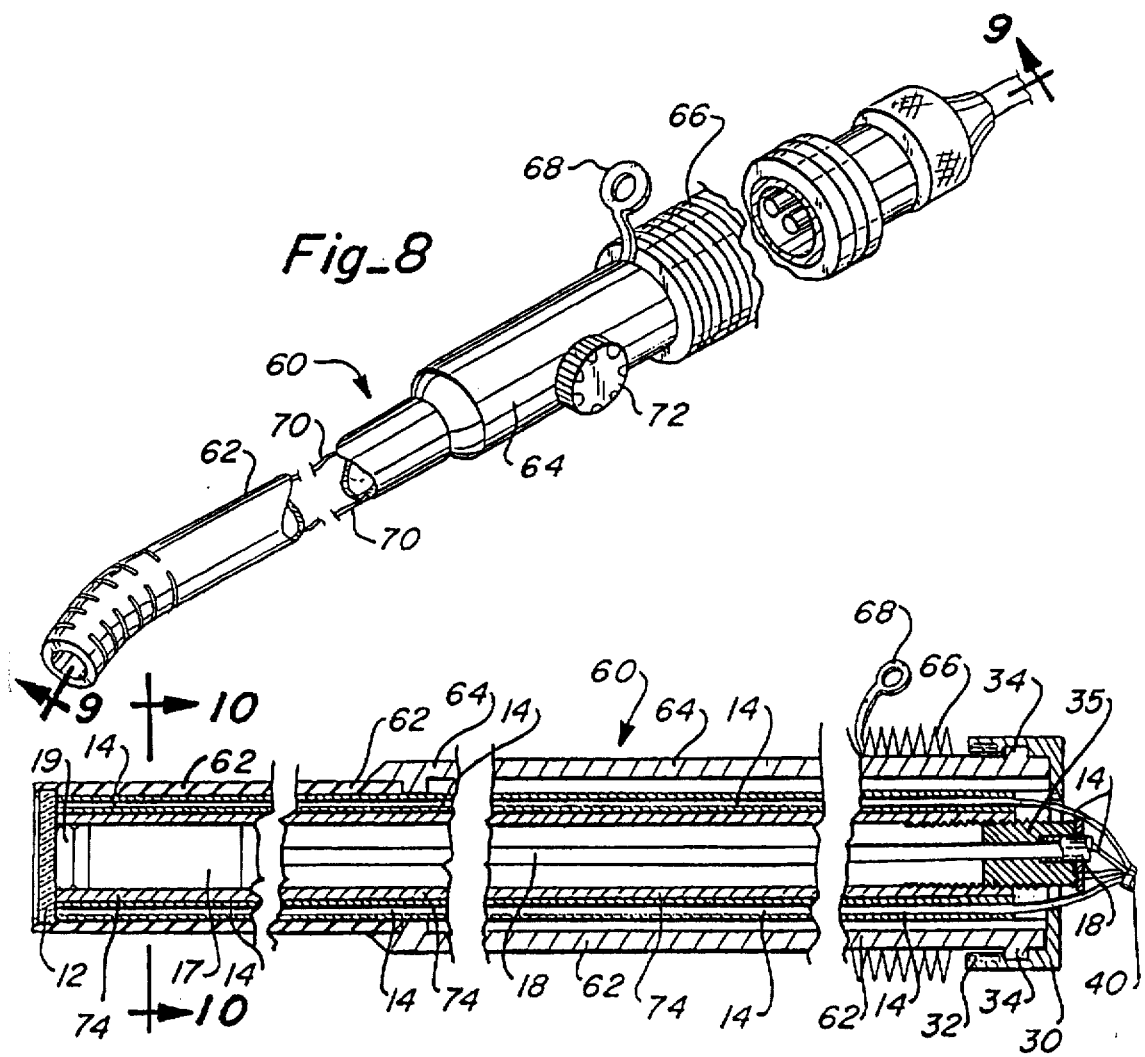
Fig_8
Fig_9
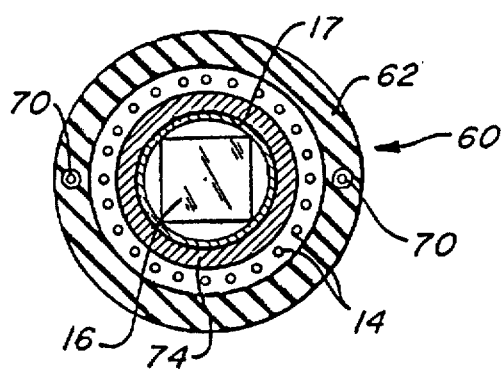
Fig_10

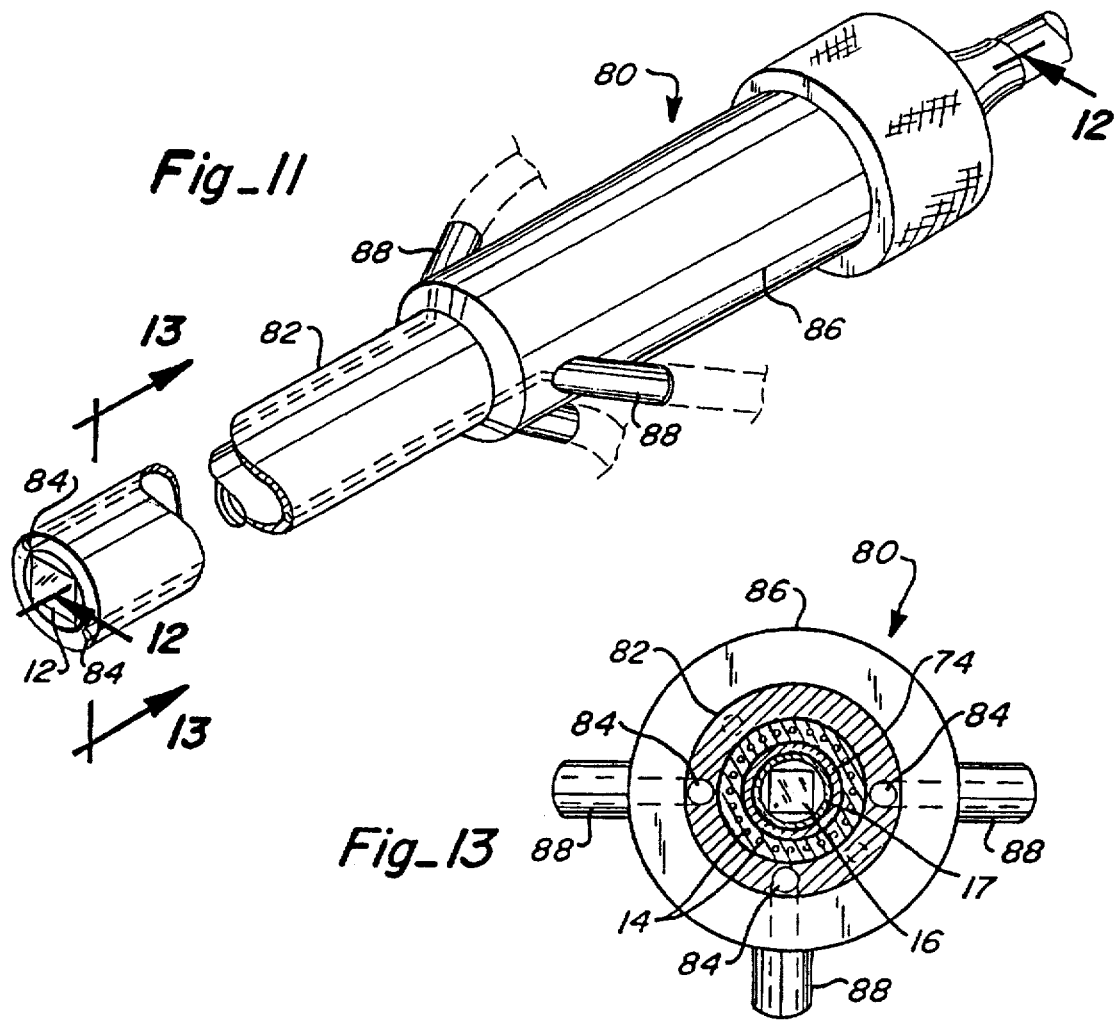
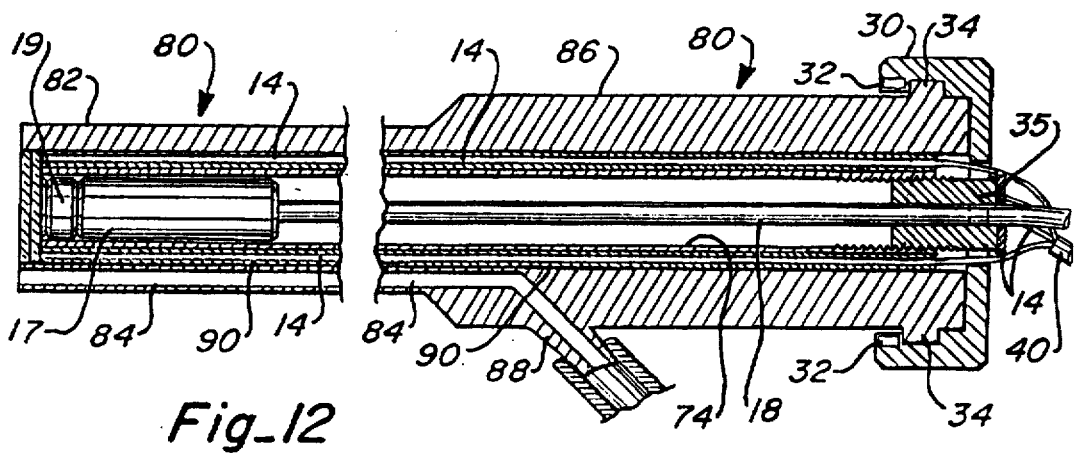

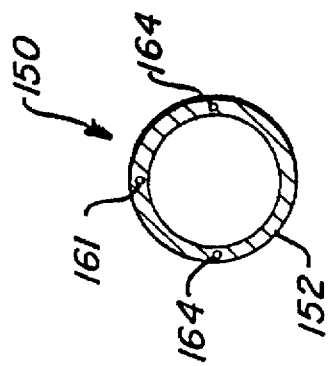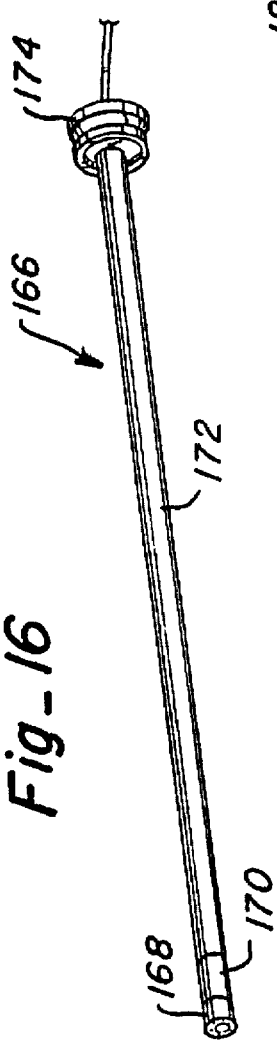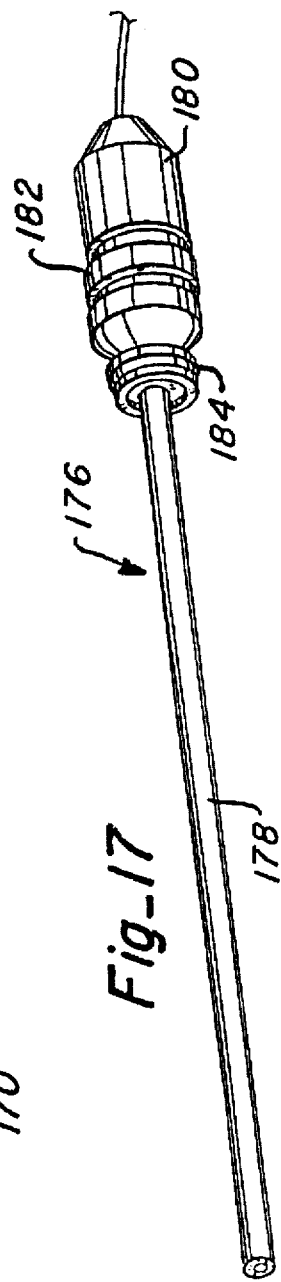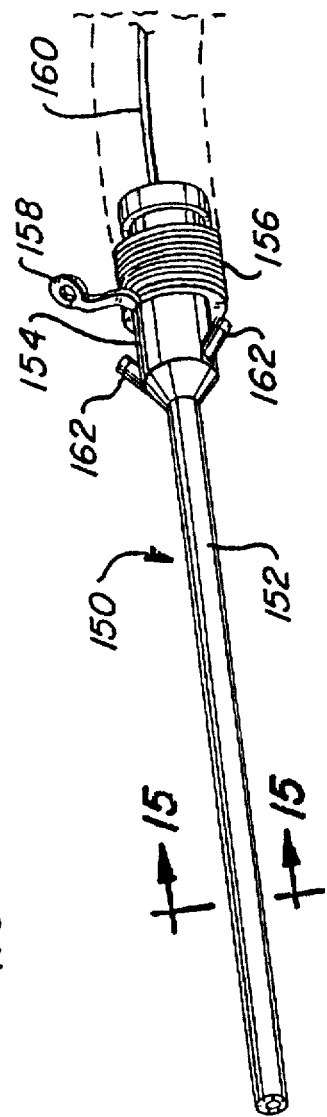

ENDOSCOPE WITH REUSABLE CORE AND DISPOSABLE SHEATH WITH PASSAGEWAYS

This application is a continuation-in-part of my U.S. patent application Ser. No. 08/080,323, filed Jun. 22, 1995, now U.S. Pat. No. 5,402,768, which is a continuation-in-part of U.S. patent application Ser. No. 07/938,629, filed Sep. 1, 1992, now abandoned.

TECHNICAL FIELD

This invention relates to an endoscope, and more particularly to a endoscope with a separable and disposable, initially sterile outer sheath containing one or more passageways and a reusable inner core which contains optics, image sensor and electronics.

BACKGROUND ART

In recent years the popularity of endoscopic surgery has proliferated. This has occurred because of the advances in technology which allow smaller and smaller endoscopes to be used, thereby permitting operative procedures to be undertaken in a less invasive manner for the patient than was previously possible. Thus, the patient suffers less trauma and recuperates much more rapidly and experiences less pain and discomfort than with more conventional surgical procedures.

Because of the sophisticated optics and electro-optics contained in modern endoscopes, they generally are very expensive. In order for this expense to be justified, they must be reused with a large number of patients.

Of course, multiple use means that the endoscope must be sterilized or at least disinfected after use with each patient prior to use with the next patient. One protocol for preoperative preparation involves immersing the endoscope in a disinfectant solution for a predetermined period of time. It is also important to flush the channels which carry gases or fluids and those channels which are used for receiving operative instruments. Another protocol is to heat sterilize the endoscope by placing it in an autoclave. However, the optics and electronics of many endoscopes will not permit them to be subjected to heat sterilization. When using the disinfectant, sometimes the endoscope is not placed in the disinfecting solution for a sufficient length of time nor are the channels flushed out completely, because of the urgency to get the endoscope back into service as soon as possible. Over time, the disinfectant solution may loose some of its strength, thereby limiting its effectiveness.

Because of these shortcomings, many studies have shown that transmission of infectious diseases from one patient to another has occurred in many instances. By way of example, transmission of salmonella typhi has been reported. In addition, pseudomonas aeruginosa has been linked to endoscopy. Also, an outbreak of serratia marcescens has been associated with the use of a bronchoscope. Furthermore, hepatitis B has been transmitted by endoscopes when the endoscopes were processed in an inappropriate manner between patients. Finally, with respect to endoscopes used on AID's patients it has been found that the sterilizing procedures have not always removed contamination of the human immunodeficiency virus (HIV). This list is not exhaustive by any means.

A high-level of disinfection failures among gastrointestinal endoscopes have been noted, as well as failures in bronchoscopes, laryngoscopes and other devices. This may be due to the fact that they are long and narrow and have long and narrow channels which are difficult to clean.

From the foregoing, it is apparent that endoscopes which can be more easily and effectively sterilized are needed.

DISCLOSURE OF THE INVENTION

In accordance with the present invention, an improved endoscope in one configuration has been provided which includes an elongated cylindrical core which includes a cylindrical housing with an objective lens within the housing or at the distal end thereof. An image sensor and associated electronics, e.g., a circuit board, is slidably mounted adjacent the objective lens within the housing. A transmitting electronic cable with multiple conductors each have a distal end connected to the image sensor electronics and a proximal end connected to a video control unit. From the video control unit signals are transmitted to the video monitor which displays the image in black and white or color. A separable outer cylindrical sheath, which is provided in a sterile condition, removably receives the core in a defined relationship and the sheath has at least one longitudinal channel for transmitting fluids or for receiving an operative instrument or carrying a light transmitting fiber. A flexible or rigid tube is connected to the proximal end of the channel for supplying fluid or for manipulating the operative instrument from a remote location. The separable sheath is disposable after use on a patient and the core is prepared for reuse with another sterile sheath on the next patient. Light transmitting fibers can be integral with the core or inserted in one of the channels in the sheath.

Optionally, a connection may be provided at the distal end of the housing for selective mounting of lens attachments which may provide straight ahead or angled fields of view. This selection of lenses are mounted outside of the sealed terminal window of the device.

In addition, either a rod inside of a tube or two thin walled concentric tubes extend proximally from the housing, or core, with electronic cables extending through the hollow interior of the core. Conveniently, the rod or tubes can have a connecting means releasably interconnecting the proximal end of the rod or tubes to the proximal end of the sheath. This connection may be accomplished by a plurality of threads or by a bayonet attachment or by other means.

The threaded tube within a tube, or the rod within a tube, allows attachment of the outer layer of the core to the objective lens. The inner tube or rod is then attached to the CCD device allowing the threads to be used to either separate the lens from the CCD device or to bring them together. This arrangement allows the device to have a sharp focusing capability. Longitudinal movement of the CCD in relationship to the optic lens is essential to obtaining sharp focus.

BRIEF DESCRIPTION OF THE DRAWINGS

FIG. 1 is a perspective view of an endoscope having a reusable core within a throwaway or disposable sheath;

FIG. 2 is an enlarged, fragmentary, horizontal section, taken along line 2—2 of FIG. 1, showing additional details of the core and sheath;

FIG. 3 is a vertical section, taken along line 3—3 of FIG. 2, showing additional details of the core and sheath;

FIG. 4 is a vertical section, taken along line 4—4 of FIG. 2, showing still further details of the core and sheath;

FIG. 5 is an enlarged, fragmentary, longitudinal section of an endoscope showing a removable lens assembly;

FIG. 6 is an enlarged, fragmentary, longitudinal section showing an end cap and a focusing member;

FIG. 7 is a vertical section, taken along line 7—7 of FIG. 6, showing further details of the end cap;

FIG. 8 is a fragmentary perspective view of an alternative endoscope embodiment having steering means;

FIG. 9 is an enlarged, fragmentary, longitudinal section, taken along line 9—9 of FIG. 8, showing further details of the endoscope;

FIG. 10 is a vertical section, taken along line 10—10 of FIG. 9, showing additional details of the endoscope;

FIG. 11 is a fragmentary, perspective view of a further alternative embodiment having operative channels in the sheath;

FIG. 12 is a fragmentary, longitudinal section, taken along line 12—12 of FIG. 11, showing further details of the endoscope;

FIG. 13 is a vertical section, taken along line 13—13 of FIG. 11, showing additional details of the endoscope;

FIG. 14 is a perspective view of a still further embodiment of a disposable sheath forming a part of an endoscope;

FIG. 15 is an enlarged cross section, taken along line 15—15 of FIG. 14, showing details of the construction of the sheath; and FIG. 16 shows one form of core for use with the sheath of FIG. 14; and FIG. 17 shows second form of core for use with the sheath of FIG. 14.

BEST MODE FOR CARRYING OUT THE INVENTION

One form of the endoscope 10 of the present invention is shown in FIGS. 1–7 wherein a throwaway channel section in the form of a cylindrical sheath 11 has a hermetically sealed window 12 at its distal end. A plurality of peripherally spaced longitudinal channels are provided in the side wall of sheath 11 for receiving light fibers 14, as shown. A cylindrical housing or core 15 is removable and slidably receivable within sheath 11. A CCD 16 is fixedly mounted within a housing 17 which contains the electronics for the CCD. An objective lens 19 is hermetically sealed in the distal end of core 15 for propagating the electronic signals through rigid cable 18 that extends from the proximal end of housing 17. Cable 18 extends through a passageway 20 in a rod portion 22 formed at the proximal end of core 15, as best seen in FIG. 2. Housing 17 is moveable longitudinally by focusing member 35 which is fixedly attached to cable 18 and threadably attached to rod portion 22 of core 15. By turning focusing member 35, rigid cable 18 causes housing 17 to be movable either closer to or further away from objective lens 19. This in-and-out capability allows separation of the CCD 16 from the objective lens 19 and thereby provides for focusing of an image at the operative site on the CCD. Cable 18 is connected to a camera control unit 24 which in turn is connected to a video monitor 26 by means of a cable 28. An end cap 30 has a pair of slots 32 which align with a pair of oppositely spaced tabs 34 on the proximal end of sheath 11 for attachment to hold rod section 22 in position within sheath 11. The end cap has a central opening 36 through which cable 18 and light fibers 14 extend. The end cap can be rotated so that each tab 34 is displaced from its respective slot 32 into a peripheral groove 38 formed in the end cap. Light fibers 14, after they exit end cap 30, are bundled into a cable 40 which connects to a light source 42, shown in FIG. 1. It will be noted, that both light fibers 14 and electronic cable 18 both exit through an opening in the cap enclosure 30. Although the drawing is done to show both detail on light fibers and electronic cable, it will be appreciated by those familiar with the technology that these cables actually exit through a water tight plastic strain relief to seal the system against water entry and to provide longer life to the two cables, i.e., light and electronic.

Conveniently, adjacent the proximate end of sheath 11 is a plastic cover 44 which is formed into an accordion shape and is connected to sheath 11, as by a ring 46. The cover 44 can be extended along the cables by pulling on pull tab 48 to pull cover 44 back over end cap 30 and down along cables 18 and 40.

It will be understood that core 15 may have been sterilized or disinfected by soaking or other means which do not require extremely high temperatures, so as not to damage the electronics. However, these methods are not always one-hundred percent effective and require long periods of time to accomplish. Just prior to use, the endoscope will be inserted into sterile sheath 11, as previously described, and cover 44 will be pulled down along cables 18 and 40. Thus, the entire portion of the endoscope inserted in the patient or associated with the patient will be completely sterile. After use, sheath 11 will be removed and thrown away and a new sterile sheath will be used for the next operative procedure. The distal end of sheath 11 can be modified, as shown in FIG. 5, to have internal threads 50 for receiving a threaded lens assembly 52, whereby the internal threads 50 provide a point of attachment which is delimited by the circumference of elongated cylindrical core housing 15. This lens assembly can be constructed to allow straight ahead viewing with various fields of view, but it can also be made to allow angled viewing at 30°, 45°, 70° or any desired angle. This terminal lens may also be an optical filter, which may be removable.

An alternative embodiment is shown in FIGS. 8–10 wherein the endoscope has a throwaway sheath 60 which is provided with a distal flexible tubular portion 62 and a proximal rigid cylindrical channel section 64 connected together as shown. Light fibers 14 and window 12 are attached to sheath 60, and are thrown away with sheath 60 after use. As in the previous embodiment, a cover 66 is provided which is in accordion configuration and has a pull tab 68 for pulling it down over the cables of the device. Sheath 60 is provided with a pair of steering wires 70 extending longitudinally through the wall of tubular section 62, as shown in FIG. 10, to a control 72 in cylindrical section 64, which works in a conventional manner for pushing or pulling the respective wires 70 to articulate the distal end of tubular section 62. If desired, a second pair of wires can be provided along with a second control for articulation in the opposite direction, all of which is well understood in the art. As in the previous embodiment, electronic housing 17 has a electronic cable 18 extending from the proximal end thereof through the opening in end cap 30. In this embodiment, the electronic housing 17 is received in the distal end of a core in the form of longitudinal tube 74 and the electronic wires extend longitudinally therethrough. It will be understood that this embodiment works just as the previous embodiment in respect to the placing the electronic housing with its associated tube 74 within the sheath 60 and holding it in position by means of end cap 30. Furthermore, it will be understood that, as in the previous embodiment, the CCD 16 is slidably mounted within housing 17 with objective lens 19 hermetically sealed in the distal end of core 74. Additionally, as in the previous embodiment, the distal end of core 74 can be modified to include threaded lens assembly 52. The sheath is sterile before use and after use is disposed of and a new sterile sheath is used with the core 74 next time the endoscope is to be used on a patient.

A further alternative endoscope which has a sheath 80 is disclosed in FIGS. 11–13, wherein the sheath has a distal section 82 with operating channel passageways 84 extending longitudinally through the side walls. The distal cylindrical channel section 82 is formed integrally with a proximal section 86 having ports 88 in communication with passageways 84. This sheath is used when the light fibers for illumination are integral with the electronic housing. As best seen in FIG. 12, housing 17 is provided within a sleeve 90 having longitudinal light fibers 14 extending therethrough. This embodiment incorporates the same structure as the previous embodiments with respect to the CCD 16, the housing 17, the lens 19, and the lens assembly 52 which may be added by modifying the core 74 in a similar fashion as shown in FIG. 5.

FIGS. 14–17 further embodiments include sheath 150 which has a distal end section 152 and a proximal end section 154 which is larger than the distal portion and is integrally formed therewith, as shown. An accordion sleeve 156 is attached adjacent the proximal end of section 154 and has a pull tab 158 for pulling it down along a light cable 160. Conveniently, the distal end of light cable 160 is connected to the proximal end of section 154 and communicates with light fiber channel 161, as best seen in FIG. 15. Additionally, section 154 has one or more inlet ports, such as inlet ports 162 which communicate with irrigation channels 164, shown in FIG. 15. The sheath 150 is adapted to receive either of the core members shown in FIGS. 16 and 17. Core 166, shown in FIG. 16, has an objective lens 168, a CCD 170 and a cable 172 connected in series as shown. The proximal end of cable 172 is connected to a locking mechanism 174 which is receivable and can be securely locked within the proximal end of section 154 of sheath 150.

Similarly, core member 176, as shown in FIG. 17 has a rod lens 178 connected at its proximal end to a camera 180 by means of a coupler 182. A locking mechanism 184 is connected between rod lens 176 and coupler 182 and is identical to locking mechanism 174 for locking into the proximal end of section 154 of sheath 150. Thus, it can be seen that cores 166 and 176 are interchangeable for use with the same sheath.

It will be understood that the embodiments in FIGS. 14–17 incorporate the same structural features as the previous embodiments with reference to a slidable CCD 168, an objective lens (not shown), and a threaded lens assembly 52 which may be added by modifying the respective core members 166 and 176 or sheath 150.

This invention has been described in detail with reference to particular embodiments thereof, but it will be understood that various other modifications can be effected within the spirit and scope of this invention.

I claim:

1. An improved endoscope having a sterilizable or fluid immersible optical section and a throwaway sterile outer sheath channel section, said endoscope comprising:

an elongated cylindrical core housing, having a distal end and a proximal end, with optical lens means mounted in said distal end thereof;

an image sensor slidably received into said proximal end of said cylindrical core housing and slidable into said distal end of said cylindrical core housing adjacent to said optical lens means;

an electronic cable having a distal end connected to said image sensor and extending proximally from said cylindrical core housing for transmitting electronic signals from said image sensor to a video control unit and then to a remote image display device;

a cylindrical channel section having a cylindrical wall having a distal end and a proximal end, and with a transparent window at said distal end thereof, and having a central passageway for receiving and positioning said cylindrical core housing with said image sensor and said optical lens means adjacent said window, and having a plurality of longitudinal channels integrally disposed within and around a portion of the circumference of said cylindrical wall, communicating with said distal end thereof; and means for releasably connecting said housing to said channel section, said channel section being disposable after use on a patient and said housing being sterilizable or soakable for reuse with another new sterile channel section on the next patient.

2. Apparatus, as claimed in claim 1, wherein:
   said channel is usable for transmitting fluids or for receiving an operative instrument.

3. Apparatus, as claimed in claim 1, further including:
   at least one light transmitting fiber in said housing with a distal end adjacent to said image sensor for transmitting light to a site under investigation from a remote light source.

4. Apparatus, as claimed in claim 1, further including:
   a light fiber extending through at least one of said plurality of channels for transmitting light to a site under investigation from a remote light source.

5. Apparatus, as claimed in claim 4, further including:
   steering wires extending through at least some of said channels for steering said channel section and said housing.

6. Apparatus, as claimed in claim 1, further including:
   an optical attachment mounted at said distal end of said housing.

7. Apparatus, as claimed in claim 6, wherein:
   said optical attachment is a lens.

8. Apparatus, as claimed in claim 6, wherein:
   said optical attachment is an elongated steerable device having a flexible distal end and a proximal end attached to said connection.

9. Apparatus, as claimed in claim 8, further including:
   light fibers means extending longitudinally through said steering device for providing light to said distal end of said steering device to provide illumination to a site under investigation.

10. Apparatus, as claimed in claim 1, further including:
    a rod having a distal end connected to said proximal end of said housing and extending proximally from said housing and having a proximal end, said electronic cables extending longitudinally through said rod, said connecting means releasably interconnects said proximal end of said rod to said proximal end of said channel section.

11. Apparatus, as claimed in claim 1, further including:
    a tube having a distal end connected to said proximal end of said housing and extending proximally from said housing and having a proximal end, said electronic cables extending longitudinally through said tube, said connecting means releasably interconnects said proximal end of said tube to said proximal end of said channel.

12. Apparatus, as claimed in claim 1, further including:
    focusing means connected to said image sensor for sliding said image sensor longitudinally with respect to said optical lens means to focus an image on said image sensor.

13. Apparatus, as claimed in claim 12, wherein said focusing means comprises:

a member fixedly connected to said proximal end of said core housing and threadably connected to said proximal end of said channel section so that by rotating said member relative to said channel section, said optical sensor is moved relative said optical lens for focusing an image on said image sensor.

14. Apparatus, as claimed in claim 1, wherein:

said channels are usable for transmitting fluids or for receiving an operative instrument.

15. Apparatus, as claimed in claim 14, further including:

at least one light transmitting fiber in said housing with a distal end adjacent to said image sensor for transmitting light to a site under investigation from a remote light source.

16. Apparatus, as claimed in claim 1, further including:

an optical attachment mount at said distal end of said channel section, said optical attachment being attached to said channel section wherein the point of attachment is delimited by a circumference of the elongated cylindrical core housing.

17. Apparatus, as claimed in claim 16, wherein:

said optical attachment is an elongated steerable device having a flexible distal end and a proximal end attached to said connection.

18. Apparatus, as claimed in claim 17, further including:

light fibers means extending longitudinally through said steering device for providing light to said distal end of said steering device to provide illumination to a site under investigation.

19. Apparatus, as claimed in claim 1, further including:

a focusing member threadably connected to said proximal end of said core housing and fixedly connected to said electronic cable so that by rotating said member relative to said core housing, said optical sensor is moved relative said optical lens for focusing an image on said image sensor.

20. Apparatus, as claimed in claim 1, further including:

steering wires extending to at least some of said channels for steering said channel section and said housing.

* * * * *